United States Patent
Holmes (10) Patent No.: US 7,851,517 B2
(45) Date of Patent: Dec. 14, 2010

(54) ANTIMICROBIAL CREDIT CARDS, IDENTIFICATION CARDS, MEMBERSHIP CARDS AND IDENTIFICATION BADGES AND BADGE HOLDERS

(76) Inventor: Lisa Marie Holmes, 902 Wildwood Cir., Grapevine, TX (US) 76051

( * ) Notice: Subject to any disclaimer, the term of this patent is extended or adjusted under 35 U.S.C. 154(b) by 360 days.

(21) Appl. No.: 11/932,764

(22) Filed: Oct. 31, 2007

(65) Prior Publication Data

US 2008/0279959 A1 Nov. 13, 2008

Related U.S. Application Data

(60) Provisional application No. 60/916,780, filed on May 8, 2007.

(51) Int. Cl.
| | |
|---|---|
| *A45C 11/18* | (2006.01) |
| *G06K 19/06* | (2006.01) |
| *A01N 59/16* | (2006.01) |
| *A01N 43/78* | (2006.01) |
| *A01N 43/80* | (2006.01) |
| *A01N 47/22* | (2006.01) |
| *A01N 43/653* | (2006.01) |
| *A01N 43/52* | (2006.01) |
| *A01N 43/64* | (2006.01) |

(52) U.S. Cl. .......... 523/122; 206/39; 235/492; 235/493; 235/494; 424/618; 514/241; 514/365; 514/372; 514/383; 514/394; 514/506; 514/721

(58) Field of Classification Search ............ 523/122; 424/618; 206/39; 235/492, 493, 494; 514/241, 514/365, 372, 383, 394, 506, 721
See application file for complete search history.

(56) References Cited

U.S. PATENT DOCUMENTS

| | | | |
|---|---|---|---|
| 2005/0175712 A1* | 8/2005 | Jayet-Laraffe et al. | 424/618 |
| 2006/0060101 A1* | 3/2006 | Nasser | 101/483 |
| 2006/0257662 A1* | 11/2006 | Bujard et al. | 428/404 |

* cited by examiner

*Primary Examiner*—Kriellion A Sanders
(74) *Attorney, Agent, or Firm*—Chalker Flores, LLP; Daniel J. Chalker; Edwin S. Flores (57) ABSTRACT

A system, method and apparatus provices an antimicrobial card, badge holder or token made from an antimicrobial polymereric material. The antimicrobial polymereric material includes one or more polymers and one or more antimicrobial agents that affect the growth of bacteria, fungi, virus or a combination thereof.

34 Claims, 4 Drawing Sheets

ANTIMICROBIAL CREDIT CARDS, IDENTIFICATION CARDS, MEMBERSHIP CARDS AND IDENTIFICATION BADGES AND BADGE HOLDERS

CROSS-REFERENCE TO RELATED APPLICATIONS

This application claims priority to U.S. Provisional Application Ser. No. 60/916,780, filed May 8, 2007, entitled, "Antimicrobial Credit Cards, Membership Cards and Identification Badges And Badge Holders," which is incorporated by reference herein in its entirety.

TECHNICAL FIELD OF THE INVENTION

The present invention relates in general to the field of plastics and plastics coatings, more particularly to antimicrobial coatings and antimicrobial cards, badges and badge holders.

BACKGROUND OF THE INVENTION

Without limiting the scope of the invention, its background is described in connection antimicrobial polymeric materials, for use in cards, credit cards, membership cards, identification badges, badge holders and antimicrobial coatings.

In the past years, there has been considerable interest in reducing the transfer of microbes and illnesses between people due in part to *E. coli* outbreaks, viral transfer and antibiotic resistant bacteria. Consequently, the market has been flooded with antimicrobial household products containing germ-killing ingredients, e.g., hand soap, hand wipes, dishwashing liquid, underwear, kitchen items, toothbrushes, toothpaste, mattresses, cutting boards, window cleaner, socks, cycling shorts, chop sticks, facial tissues and so forth. However, these materials only provide a temporary effect and are prone to becoming less effective over time as a result of reduced concentrations of antimicrobial agents.

There has been a growing interest in new antimicrobial solutions in recent years, driven by a desire to provide longer lasting protection in products that can be degraded by microbes, to control or eliminate the undesirable effects created by the presence of microbes, such as odor or discoloration. Historically, these antimicrobial effects have been delivered through conventional additives such as fungicides or bactericides; however, such additives are used in small amounts and are typically added after manufacture, and end up being indiscriminately distributed onto the surface. These additives can be lost over time due to leaching and degradation resulting from exposure to light, heat and the environment. In addition, these additives are not used on all materials and in fact are not present in many items that are routinely passed from person to person. As a result, items that are passed from person to person are more susceptible to microbe transfer.

In modern society, cards of various kinds have become ubiquitous and it is not uncommon for individuals to carry numerous cards, including credit cards, ATM or bank cards, debit cards, "smart" cards, insurance cards, a driver's license, identification cards, telephone calling cards, transit cards, library cards, discount cards and card-entry hotel keys. In addition, numerous transactions require the use of these cards numerous times a day (e.g., as the form of payment or as identification). As a result, these cards are in contact with numerous people (e.g., cashier, manager, attendant, etc.) and devices that have also been in contact with numerous other individuals. This allows the transfer of a wide variety of substances, (e.g., food, microbes, viruses, drinks, bacteria, fungus, spores, and other materials) and provides a mechanism for cross contamination of various microbes from person to person and place to place. Yet for the most part, card users do not realize that these cards can be the source of an illness. Even if they do, they are reluctant to clean or disinfect these cards for fear the cleaner or disinfectant will damage the card.

As a result, there is a need for a system, method and apparatus for a practical card or device that reduces the growth bacteria, fungi, virus or other microbes on the surface of a card.

SUMMARY OF THE INVENTION

The present invention provides a system, method and apparatus for a practical and secure card or device that reduces the growth bacteria, fungi, virus or other microbes on the surface of a card. The transfer of microbes, viruses and other sources of contamination via cards or like devices (e.g., credit cards, drivers' licenses, membership cards, hotel keys, department store cards, employee badges, name badge holders and so forth), which has been overlooked until now, can be controlled and limited by using the present invention. These items are routinely handled by numerous individuals on a daily basis. Likewise, employees in service jobs (e.g., government, hospitals, restaurants, retail stores, etc.) and security jobs can handle and be exposed to hundreds of cards per day. The integration or embedding of antimicrobial materials in these items or the raw materials during the manufacturing process provides a durable, long lasting solution to his overlooked problem. As a result, the antimicrobial card in accordance with the present invention provides a secure and flexible system for security and/or commercial transactions using access, credit, debit, identification, security, stored value and vendor-specific cards and/or devices.

More specifically, the present invention provides an antimicrobial card with one or more identifiers disposed on or within the card. The card is made from an antimicrobial polymereric material. The antimicrobial polymereric includes one or more polymers and one or more antimicrobial agents that affect the growth of bacteria, fungi, virus or a combination thereof on the antimicrobial card. The identifiers may include a barcode, a magnetic stripe, a magnetic stripe emulator, an image, a computer chip, a smart-card interface, a wireless interface, an optical interface, a communications interface, a radio frequency identification (RFID), a hologram, a logo, an identification number, a company name, a user name, an owners name, a design, an image or a combination thereof.

The present invention includes an antimicrobial card having a magnetic stripe and is made from an antimicrobial polymereric material that including one or more polymers and between about 0.05 and 3% of one or more antimicrobial agents that affect the growth a bacteria, a fungi, a virus. The one or more polymers may be selected from styrene, polyvinyl chloride and laminated polyvinyl chloride; and one or more antimicrobial agents may be selected from 2,4,4'-trichloro-2'-hydroxydiphenyl ether; silver zeolite; silver glass; 4-t-butylamino-6-cyclopropylamino-2-methylthio-s-triazine; thiabendazole; 2-(4-thiazolyl)benzimidazole; dichloro-octyl-isothiazolone; octyl-isothiazolone; 10,10-oxybisphenoxarsine; tebuconazole; tolnaftate; zinc bis-(2-pyridinethiol-1-oxide) and mixtures and combinations thereof.

The present invention provides an antimicrobial token having a token made from an antimicrobial polymereric material with one or more polymers and one or more antimicrobial agents that affect the growth of bacteria, fungi, virus or a combination thereof on the token. The token also includes one or more identifiers disposed thereon. On specific example includes a gambling chip.

The present invention also includes a method of reducing the growth of bacteria, fungi, or virus on a card by forming an antimicrobial card comprising one or more polymers and one or more antimicrobial agents and a magnetic stripe.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

As used herein the terms "card" and "credit card" are used interchangeably to generally to refers to a plastic identification card that includes credit cards and similar cards such as debit cards, insurance cards, transaction cards, supermarket cards, club cards, lost and found key chain program cards, library cards, health club cards, membership cards, rental car loyalty programs cards, hotel loyalty programs cards, prepaid phone cards, video rental cards, access cards, identification cards, drivers licenses, firearm licenses, physical access security cards, mini-cards, security cards, stored value cards, a vendor-specific cards, and the like. In addition, the size and shape of the credit card may be of any desired size. For example, cards may be credit card size 2⅛"×3⅛" with a thickness of between 10 and 35 mils thick; however, other sizes and shapes are equally acceptable and include standard cards with slot punches, baggage tags, key tags, breakaway key tags (e.g., used in a variety of loyalty, frequent shopper, and membership programs) and so forth.

The term "antimicrobial" as used herein means that the present invention inhibits, prevents, reduces or destroys the growth or proliferation of microbes such as bacteria, fungi, viruses or the like. Common antimicrobial agents as used herein includes germicides, antibacterials, antivirals, antifungals, antiprotozoals and antiparasites. The term "antiviral" as used herein means the present invention inhibits, prevents, reduces or destroys the growth or proliferation of viruses or of virally infected cells. The term "antifungal" as used herein means the present invention inhibits, prevents, reduces or destroys the growth or proliferation of fungi.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

The present inventor recognized a major source of cross contamination is from the transfer of cards and identification between individuals. For example, the present inventor recognized that there is no antimicrobial activity for a driver who hands his drivers' license to the authorities, an individual who offers his identification to a transportation safety employee at the airport, cashiers or patients who touched the badges of a healthcare provider. In addition, it is not uncommon for hotel keys, credit cards, casino cards to be put in people's mouths placed on dirty counters, or other microbe-laden places as they fumble for keys or performs other activities providing transfer of microbes from one source to another.

The present inventor recognized that by reducing the number of microbes transferred between individuals would reduce the spread of those microbes. The present invention provides for the use of antimicrobial agents incorporated in the material itself or applied to the surface of commonly transferred items that are handled by numerous different people throughout the day. Such items commonly include credit cards, drivers' licenses, membership cards, hotel keys, dept. store credit cards, employee badges, name badge holders and other similar items. Note that the present invention is also applicable to casino chips, tokens and other polymer-based products. As a result, the present invention provides a system, method and apparatus for a practical and secure card or device that reduces the growth bacteria, fungi, virus or other microbes on the surface of a card.

The present invention provides antimicrobial polymers that either have inherent antimicrobial characteristics, or incorporate a conventional antimicrobial additive encapsulated or embedded into a polymer. Embedding the antimicrobial agent in the polymer composition of the article and/or in a coating applied to the article provides long-term antimicrobial activity for an article. Since the antimicrobial agent or part of the molecule that is primarily responsible for the antimicrobial action is attached to a polymer or uniformly embedded into the polymer at a nanoscopic level, these antimicrobial agents provide a more sustained and effective antimicrobial action over time than can be achieved by other means. This antimicrobial activity can be provided through a variety of methods depending on the antimicrobial agent used. For example, an antimicrobial agent may interact with the cell wall of a microbe to penetrate the cell or disrupt one or more cellular functions. This may cause the microbes to be unable to function, grow and/or reproduce. In other embodiments, the antimicrobial activity may be rechargeable.

Generally, conventional cards include a core stock, usually of plastic, such as polyvinyl chloride mylar or styrene and usually has an embossed surface with the name, card number and other embossed or non-embossed information, such as conditions of use. The present invention includes one or more antimicrobial agent incorporated into the plastic used to form the card.

Figure 1A:
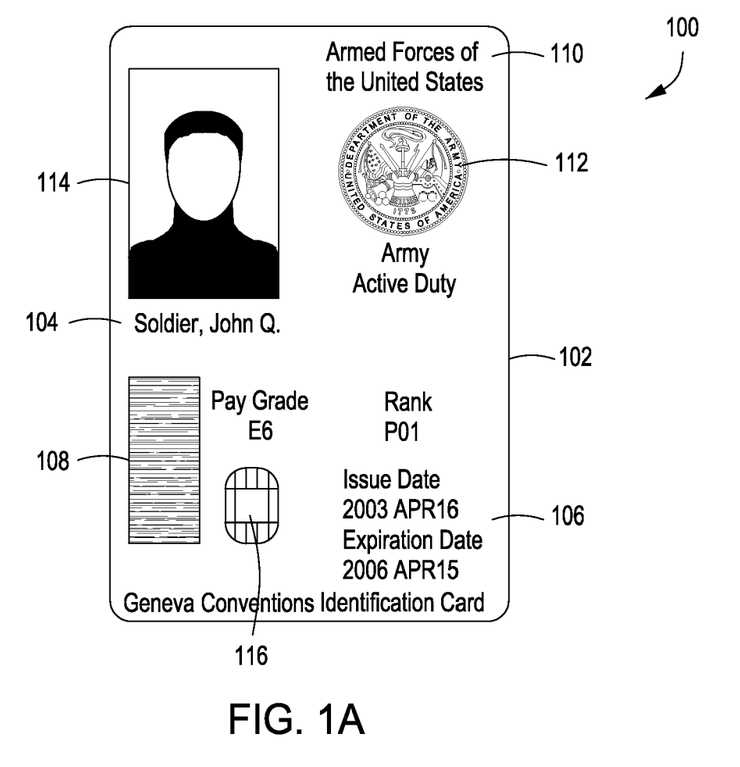
FIGS. 1A and 1B are front and back views of a polymeric antimicrobial card in accordance with one embodiment of the present invention.
Figure 1B:
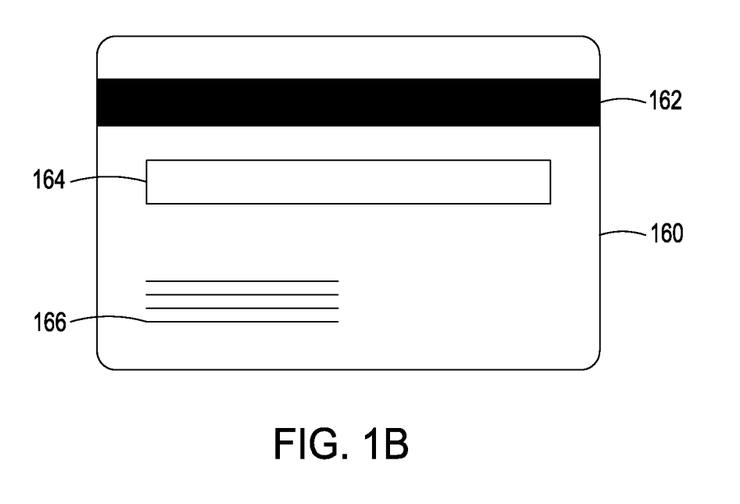

Referring now to FIG. 1A, the front 100 of an exemplary embodiment of a card having antimicrobial activity, while enabling transactions in accordance with the present invention is shown. The card 100 is shown in the form of an identification card for illustrative purposes only. The front 102 of the card 100 includes the card holder's name 104, a card number 106, an encryption region 108, the issuer's name 110, a hologram 112, an image 114 and a chip 116. Other information and features may also be placed on or within the card. As will be appreciated by those skilled in the art, the features described above can be rearranged or eliminated to fit a specific application for the card. In some instances, the cards may contain logos of various companies 112, a magnetic strip, bar code 108, an RFID, a smart-card interface (computer chip) 116 and combinations thereof or other mechanisms to contain information and/or data. Other types of identifiers may also be used, such as a magnetic stripe emulator, an image, a wireless interface, an optical interface, a communications interface, a RFID, a hologram, a design, an image or any combination thereof Now referring to FIG. 1B, the back 160 of an exemplary embodiment of a card for enabling transactions having a magnetic stripe in accordance with the present invention is shown. The back 160 of the card includes the magnetic stripe 162, an area for the card holder to place an authorized signature 164 and the issuer's contact information and disclaimers 166. Other information and features may also be placed on or within the card. As will be appreciated by those skilled in the art, the features described above can be rearranged or eliminated to fit a specific application for the card.

Figure 2A:
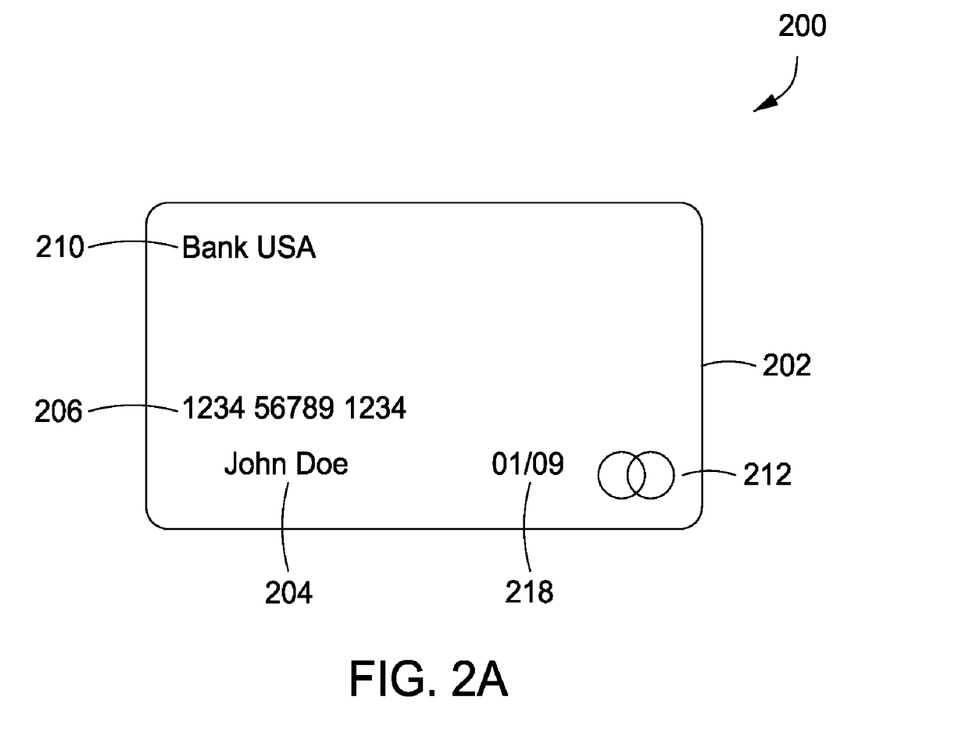
FIGS. 2A and 2B are front and back vies of a polymeric antimicrobial credit card in accordance with another embodiment of the present invention.

Referring now to FIG. 2A, the front 202 of an exemplary embodiment of a credit card having antimicrobial activity, while enabling transactions in accordance with the present invention is shown. The card 200 is shown in the form of a credit card for illustrative purposes only. The front 202 of the card 200 includes the card holder's name 204, a card number 206, the issuer's name 210, a hologram 212 and an expiration date 218. Other information and features may also be placed on or within the card. As will be appreciated by those skilled in the art, the features described above can be rearranged or eliminated to fit a specific application for the card.

Figure 2B:
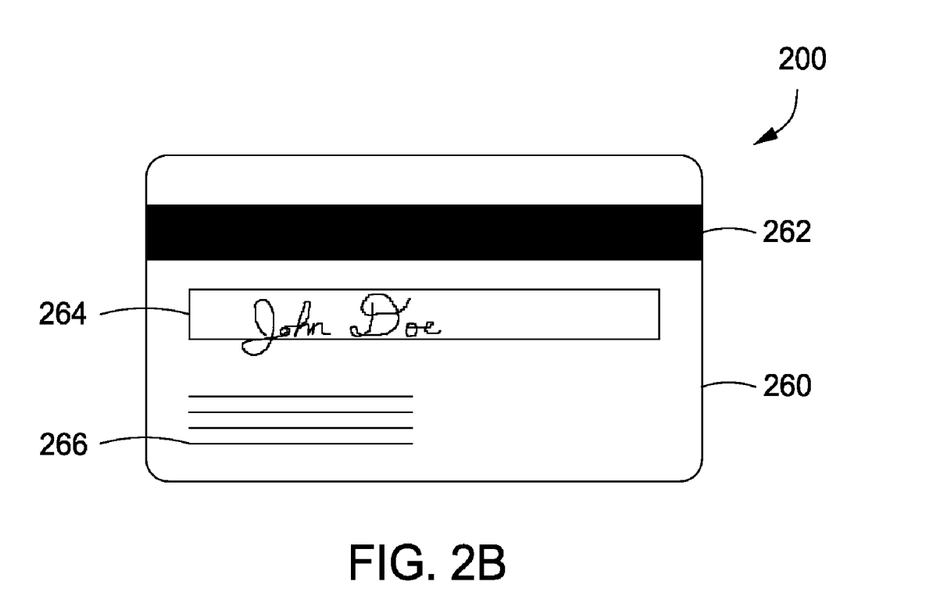

Now referring to FIG. 2B, the back 260 of an exemplary embodiment of a polymeric antimicrobial card 200 for enabling transactions having a magnetic stripe in accordance with the present invention is shown. The back 160 of the card includes the magnetic stripe 262, an area for the card holder to place an authorized signature 264 and the issuer's contact information and disclaimers 266. Other information and features may also be placed on or within the card. As will be appreciated by those skilled in the art, the features described above can be rearranged or eliminated to fit a specific application for the card.

Figure 3A:
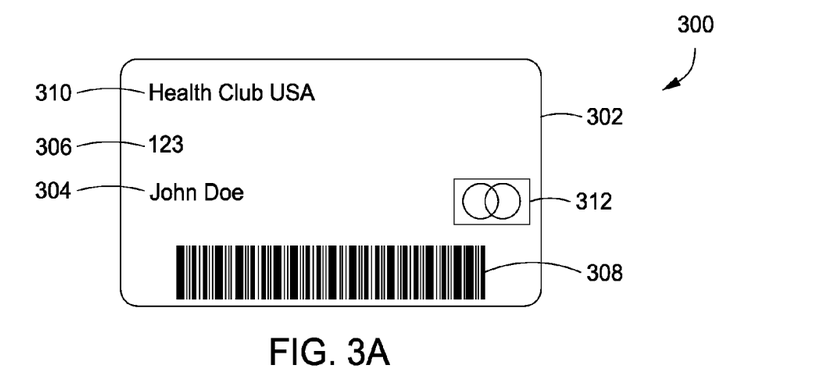
FIGS. 3A to 3F illustrate different embodiments of cards having antimicrobial activity in accordance with the present invention.

Referring now to FIGS. 3A to 3E, different exemplary embodiments of cards having antimicrobial activity are illustrated. FIG. 3A is membership card 300 having a front 302 that includes the card holder's name 304, a card number 306, the issuer's name 310, a hologram 312 and a barcode 108.

Figure 3B:
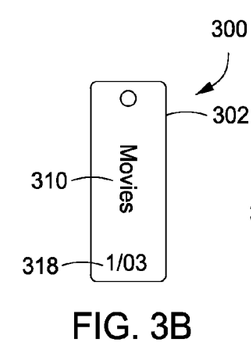
Figure 3C:
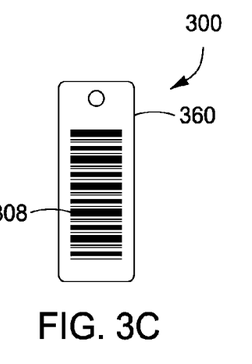

FIG. 3B is a mini-card 300 for use on key rings and other hand held rings. The information displayed on the front 302 of mini-card 300 may include a variety of information in addition to the issuer's name 310 and expiration date 318. FIG. 3C is the back 360 of a mini-card 300 for use on key rings. The information displayed may include a variety of information in addition to the barcode 308.

Figure 3D:
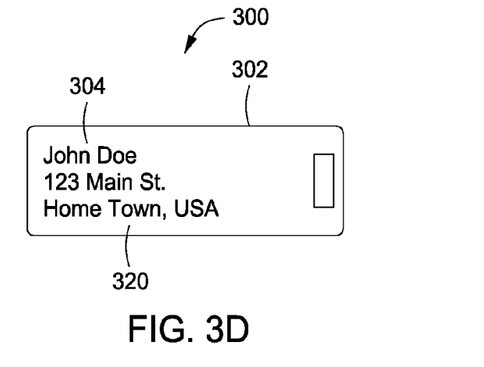

FIG. 3D is a luggage tag 300 for use on luggage during travel. The information displayed on the front 302 may include a variety of information including the owner's name 304 and address 320. The luggage tag 300 may include other information as necessary, e.g., logo, company name, barcode, image, picture, etc. (not shown).

Figures 3E, 3F:
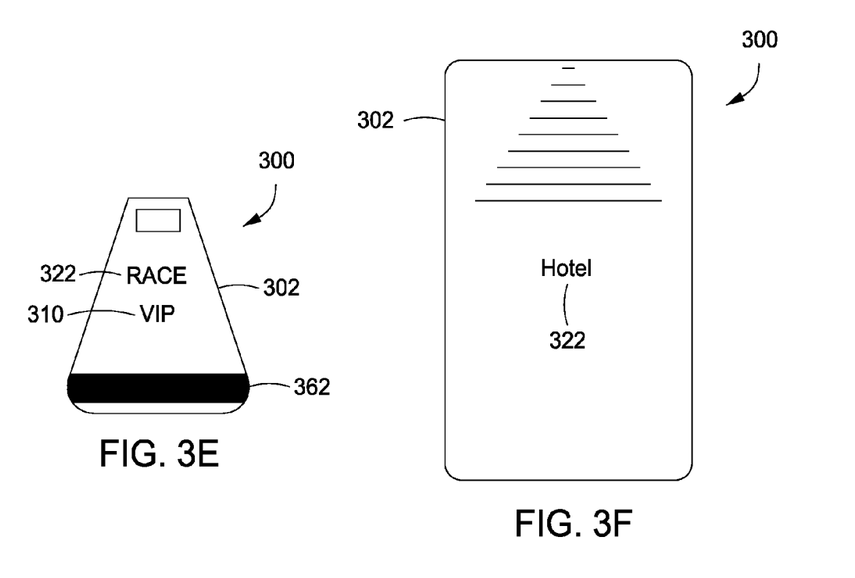

FIG. 3E is a pass 300 for use at a venue or event. The information displayed on the front 302 may include a variety of information including the issuer's name 310, magnetic stripe 362, and event name 322. The luggage tag 300 may include other information as necessary, e.g., logo, company name, barcode, image, picture, etc. (not shown).

FIG. 3F is a hotel key 300 for use to open doors and gates. The information displayed on the front 302 may include a variety of information including the logo, company name, hotel name 322.

Figure 4A:
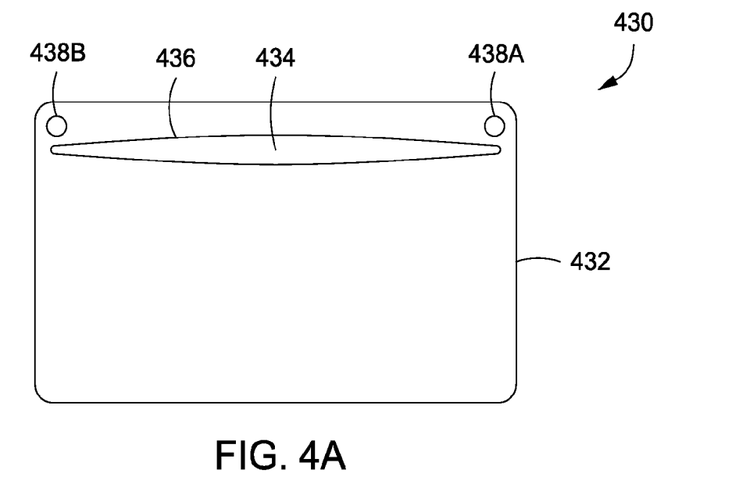
FIGS. 4A and 4B illustrate a polymeric antimicrobial badge holders in accordance with yet another embodiment of the present invention.

FIG. 4A is a polymeric antimicrobial badge holder 430 having a front 432 and a back 434 with a slot 436 in the front 432 to allow access to the interior of the badge holder 430 for placing a card (not shown). The badge holder 430 may also include attachment holes 438a and 438b to position a tie (not shown) to allow positioning about the user.

Figure 4B:
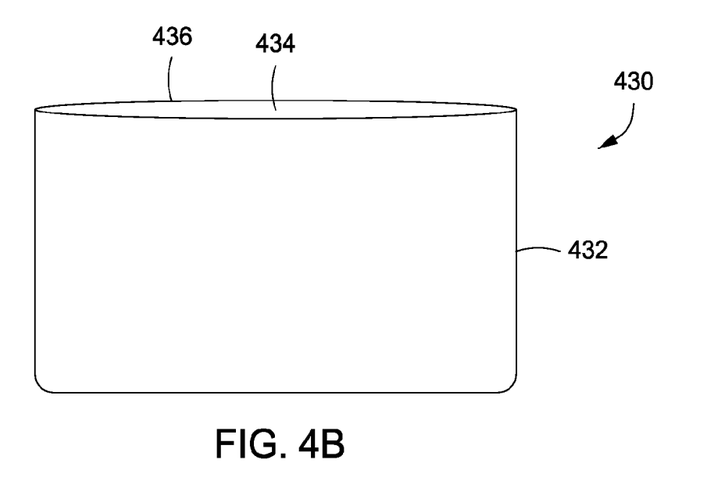

FIG. 4B is another embodiment of a polymeric antimicrobial badge holder 430 having a front 432 and a back 434 with a slot 436 in the front 432 to allow access to the interior of the badge holder 430 for placing a card (not shown). The polymeric antimicrobial badge holder 430 may also include a clip, pin, tape, loop and hook, or magnet to secure the polymeric antimicrobial badge holder 430 to the area.

Figure 5:
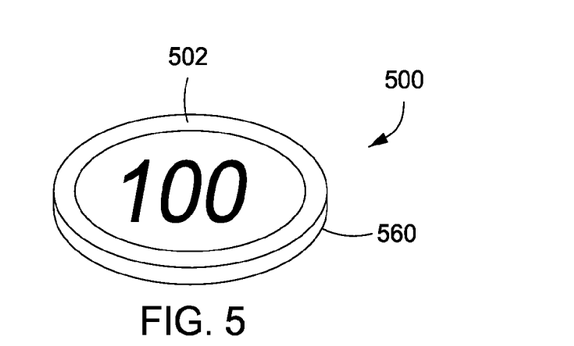
FIG. 5 illustrates a polymeric antimicrobial token.

Now referring to FIG. 5 is an illustration of an antimicrobial token 500. The antimicrobial token 500 includes a token back 502 and token front 560 with the antimicrobial token 500 being made from an antimicrobial polymereric material with one or more polymers and one or more antimicrobial agents that affect the growth of bacteria, fungi, virus or a combination thereof on the token. The antimicrobial token 500 also includes one or more identifiers disposed thereon and in some embodiments the antimicrobial token 500 will be a gambling chip. The skilled artisan will recognize that other information and features may also be placed on or within the antimicrobial token 500. As will be appreciated by those skilled in the art, the features described above can be rearranged or eliminated to fit a specific application for the antimicrobial token 500.

Other embodiments of the present invention include a card having a polymer cover or polymer coating such as a transparent polyvinyl chloride film or a coating such as acrylic polymer that includes one or more antimicrobial agents incorporated therein and positioned over the card. Still other embodiments of the present invention include cards made of plastics or polymers that include one or more antimicrobial agents and are covered by a polymer cover or polymer coating that includes one or more antimicrobial agents incorporated therein and positioned over the card. In addition, the materials described herein can be used as card or badge holders.

The skilled artisan will recognize that any polymer may be used provided it is compatible with the selected antimicrobial agent and may be in the form of films, foams, molded parts, pellets, sheets, fibers, fabrics, slabs or coatings. The polymer products are synthetic or natural or are blends of synthetic and natural products. For example, the polymer used in the present invention may include acrylonitrile-butadiene-styrene, allyl resin, cellulosic, epoxy, ethylene vinyl alcohol, fluoroplastics, (PTFE), (FEP, PFA, CTFE, ECTFE, ETFE), liquid crystal polymer, melamine formaldehyde, phenolformaldehyde plastic, polyacetal, polyacrylates, polyacrylonitrile, polyamide, Nylon, polyamide-imide, polyaryletherketone, polybutadiene, polybutylene, polycarbonate, polydicyclopentadiene, polyektone, polyester, polyetheretherketone, polyetherimide, polyethersulfone, polyethylene, polyethylenechlorinates, polyimide, polymethylpentene, polyphenylene oxide, polyphenylene sulfide, polyphthalamide, polypropylene, polystyrene, polysulfone, polyurethane, polyvinylchloride, polyvinylidene chloride, silicone, thermoplastic elastomers, carboxyl-containing ethylene copolymers and combinations and mixtures thereof.

When the present invention includes polymers formed from one or more monomers, the monomers used singly or a plurality and in the case of copolymerization, both random copolymerization and block copolymerization may be employed. Monomer include (meth)acrylic acid, methyl (meth)acrylate, ethyl(meth)acrylate, n-propyl(meth)acrylate, isopropyl(meth)acrylate, n-butyl(meth)acrylate, isobutyl (meth)acrylate, tert-butyl (meth)acrylate, n-pentyl(meth) acrylate, n-hexyl(meth)acrylate, cyclohexyl(meth)acrylate, n-heptyl(meth)acrylate, n-octyl(meth)acrylate, 2-ethylhexyl (meth)acrylate, nonyl (meth)acrylate, decyl(meth)acrylate, dodecyl(meth)acrylate, phenyl(meth)acrylate, toluoyl (meth) acrylate, benzyl(meth)acrylate, 2-methoxyethyl(meth)acrylate, 3-methoxybutyl (meth)acrylate, 2-hydroxyethyl(meth) acrylate, 2-hydroxypropyl(meth)acrylate, stearyl (meth) acrylate, glycidyl(meth)acrylate, 2-aminoethyl(meth) acrylate, .gamma.-(methacryloyloxypropyl) trimethoxysilane, (meth)acrylic acid-ethylene oxide adducts, trifluoromethylmethyl(meth)acrylate, 2-trifluoromethylethyl (meth)acrylate, 2-perfluoroethylethyl(meth)acrylate, 2-perfluoroethyl-2-perfluorobutylethyl(meth)acrylate, 2-perfluoroethyl(meth)acrylate, perfluoromethyl(meth)acrylate, diperfluoromethylmethyl (meth)acrylate, 2-perfluoromethyl-2-perfluoroethylmethyl(meth)acrylate, 2-perfluorohexylethyl(meth)acrylate, 2-perfluorodecylethyl(meth)acrylate and 2-perfluorohexadecylethyl(meth)acrylate; styrenic monomers such as styrene, vinyltoluene, .alpha.-methylstyrene, chlorostyrene, styrenesulfonic acid and salts thereof; fluorine-containing vinyl monomers such as perfluoroethylene, perfluoropropylene and vinylidene fluoride; silicon-containing vinyl monomers such as vinyltrimethoxysilane and vinyltriethoxysilane; maleic anhydride, maleic acid and monoalkyl esters and dialkyl esters of maleic acid; fumaric acid and monoalkyl esters and dialkyl esters of fumaric acid; maleimide monomers such as maleimide, methylmaleimide, ethylmaleimide, propylmaleimide, butylmaleimide, hexylmaleimide, octylmaleimide, dodecylmaleimide, stearylmaleimide, phenylmaleimide and cyclohexylmaleimide; nitrile-containing vinyl monomers such as acrylonitrile and methacrylonitrile; amido-containing vinyl monomers such as acrylamide and methacrylamide; vinyl esters such as vinyl acetate, vinyl propionate, vinyl pivalate, vinyl benzoate and vinyl cinnamate; alkenes such as ethylene and propylene; conjugated dienes such as butadiene and isoprene; vinyl chloride, vinylidene chloride, allyl chloride, allyl alcohol and so forth.

Specifically the present invention may be made in part from styrene or polyvinyl chloride depending on the type of finishing or printing desired. Another common material for the present invention includes laminated polyvinyl chloride, which is the most widely used material for plastic cards since it is the standard for financial transaction cards such as credit cards, ATM cards and most magnetic stripe cards and smart cards.

The present invention may also be used as a cover or coating for card to provide antimicrobial activity. The antimicrobial cover or coating may be applied by spraying, dipping, painting, wiping, bonding, fusing or other manner in order to affix a coating to the surface of a card, especially a transparent coating that covers at least a portion of the card.

The antimicrobial agents may be combined with the polymer or monomers in a variety of manners known to the skilled artisan. For example, the incorporation of the antimicrobial agents into the polymer products is performed by known methods such as dry blending in the form of a powder or wet mixing in the form of solutions, dispersions or suspensions in an inert solvent, water or oil. They may be added directly into the processing apparatus (e.g., extruders, mixers, kneaders, etc.) in an inert atmosphere or ambient atmosphere. The antimicrobial agents may be added in the form of a master batch or polymer concentrate. The application of the antimicrobial agents may be performed by applying the dissolved or dispersed agents to the polymer product with or without subsequent evaporation of the solvent or the suspension dispersion material.

The antimicrobial additives function via different mechanisms depends on the type of antimicrobial agent. For example, the antimicrobial agent may function by disrupting a biochemical pathway, the antimicrobial agent functions by breaching the integrity of the cell wall of the microbe and are less likely to contribute to development of resistance in the targeted microbes. A variety of active sites and polymer backbones can be designed to suit a given application.

The present invention provides the incorporation of antimicrobial agent into a polymer that is inherently antimicrobial or inert. The antimicrobial agent is typically incorporated during the polymerization process in such a way that it is uniformly distributed into the polymer at a nanoscopic level. This embedding of the antimicrobial agent into the polymer matrix provides complete antimicrobial agent coverage of the surface in a more uniform and consistent manner thus increasing the longevity of the antimicrobial effect. In this way, it is possible to get increased efficacy and sustainability while providing the benefits of an antimicrobial polymer.

It is also possible to use the present invention to deliver a concentrated dose of the additive into a given formulation or application, paints and coatings, where the additive is distributed into a polymeric carrier used to deliver the antimicrobial agent. This approach also makes it possible to enhance the inherently antimicrobial polymer with an antimicrobial agent by creating a "tunable" antimicrobial polymer where the activity can be selectively controlled using either the additive or the polymer as the situation demands.

The skilled artisan will recognize that numerous antimicrobial agents may be used in the present invention. The present invention provides antimicrobial polymer compositions particularly effective in a wide variety of end use applications when intimately mixed with or applied to a polymer product. The antimicrobial agents may be employed singly or in any combination in order to achieve desired results. For example, the antimicrobial agents may be zeolite (crystalline aminosilicate), clay mineral and silica gel, zirconium phosphate, calcium phosphate, silver, benzotriazole type compounds (e.g., 2-(5-methyl-2-hydroxyphenyl)-benzotriazole, 2-(2-hydroxy-3,5-bis(alpha,alpha-dimethylbenzyl)-phenyl)-2H-benzotriazole, 2-(3,5-di-tert-butyl-2-hydroxyphenyl)-benzotriazole, 2-(3-tert-butyl-5-methyl-2-hydroxyphenyl)-5-chloroenzotriazole, 2-(3,5-di-tert-butyl-2-hydroxyphenyl)-5-chlorobenzotriazole and 2-(3,5-di-tert-amyl-2-hydroxyphenyl)-benzotriazole), oxalic acid anilide type compounds (e.g., 2-ethoxy-2'-ethyloxalic acid bisanilide and 2-ethoxy-5-tert-butyl-2'-ethyloxalic acid bisanilide), salicylic acid type compounds (e.g., phenyl salicylate, p-tert-butylphenyl salicylate and p-octylphenyl salicylate), cyanoacrylate type compounds (e.g., 2-ethylhexyl-2-cyano-3,3'-diphenyl acrylate and ethyl-2-cyano-3,3'-diphenyl acrylate), benzophenone type compounds (e.g., 2,4-dihydroxybenzophenone, 2-hydroxy-4-methoxybenzophenone, 2-hydroxy-4-octoxybenzophenone, 2-hydroxy-4-dodecyloxybenzophenone, 2,2'-dihydroxy-4-methoxybenzophenone, 2,2'-dihydroxy-4,4'-dimethoxybenzophenone and 2-hydroxy-4-methyoxy-5-sulfobenzophenone), hindered amine type compounds (e.g., dimethyl succinate/1-(2-hydroxyethyl)-4-hydroxy-2,2,6,6-tetramethylpiperidinepolycondensate, poly((6-(1,1,3,3-tetramethylbutyl)-imino-1,3,5-triazine-2,4-diyl) ((2,2,6,6-tetramethyl-4-piperidyl)-imino)-hexamethylene-((2,2,6,6-tetramethyl-4-piperidyl)-imino)), and bis(1,2,2,6,6-pentamethyl-4-piperidyl) 2-(3,5-di-tert-butyl-4-hydroxybenzyl)-2-n-butylmalonate), and hindered phenol type compounds (e.g., triethylene glycol bis(3-(3-tert-butyl-5-methyl-4-hydroxyphenyl)-propionate), 1,6-hexanediol bis(3-(3,5-ditert-butyl-4-hydroxyphenyl)-propionate), 2,4-bis(n-octylthio)-6-(4-hydroxy-3,5-di-tert-butylanilino)-1,3,5-triazine, pentaerythritol tetrakis(3-(3,5-di-tert-butyl-4-hydroxyphenyl)-propionate), 2,2-thiodiethylene-bis(3-(3,5-di-tert-butyl-4-hydroxyphenyl)-propionate), octadecyl 3-(3,5-tert-butyl-4-hydroxyphenyl)-propionate, 2,2-thiobis(4-methyl-6-tert-butylphenol), N,N'-hexamethylene-bis(3,5-di-tert-butyl-4-hydroxy-hydrocinnamamide), 3,5-di-tert-butyl-4-hydroxy-benzylphosphonate diethyl ester, 1,3,5-trimethyl-2,4,6-tris (3,5-di-tert-butyl-4-hydroxybenzyl)benzene, calcium (ethyl bis(3,5-di-tert-butyl-4-hydroxybenzyl-phosphonate)) and tris-(3,5-di-tert-butyl-4-hydroxybenzyl) isocyanurate).

Other antimicrobial agents include 2,4,4'-trichloro-2'-hydroxydiphenyl ether; silver zeolite or silver glass; 4-t-butylamino-6-cyclopropylamino-2-methylthio-s-triazine, CAS No. 28159-98-0; thiabendazole, 2-(4-thiazolyl)benzimidazole, CAS No. 148-79-8; dichloro-octyl-isothiazolone; octyl-isothiazolone; 10,10-oxybisphenoxarsine; tebuconazole; tolnaftate; and zinc bis-(2-pyridinethiol-1-oxide).

The skilled artisan will recognize that the concentration of antimicrobial agents may vary depending on the specific article to be protected and the specific antimicrobial agent. For example, the concentration of antimicrobial agent may range from about 0.01% to 50% or greater; however, common antimicrobial agent concentrations include 1, 2, 5, 7, 10, 15, 20, 25, 30 percent (+5 percent) or greater.

In addition to the antimicrobial action, these antimicrobial agents can provide polymer-related attributes such as binding, adhesion, barrier and bonding properties that conventional antimicrobial additives cannot. This multifunctional aspect may be of value where an ingredient is required to perform more than one function and thereby help in delivering a simpler and cost-effective solution. The intention for these new materials is thus not a direct replacement of the active ingredients used today but to provide additional benefits that cannot be provided in terms of durability, uniformity, consistency and greater functionality.

Moreover, the present invention may include an indicator that provides an indication of the level of antimicrobial activity in the card and how effective the card is at affecting the growth and proliferation of microbes. This can function as a visible indicator of the antimicrobial activity of the card and when it is time to replace the card. This indicator may be link the antimicrobial activity to a color or image present in or on the card.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. An antimicrobial card comprising:
   a card made from an antimicrobial polymereric material comprising one or more polymers and one or more antimicrobial agents that affect the growth of bacteria, fungi, virus or a combination thereof on the card such that the antimicrobial polymeric material is at least on an exterior of the card; and
   one or more identifiers disposed on or within the card.

2. The antimicrobial card as recited in claim 1, wherein the identifiers comprise a barcode, a magnetic stripe, a magnetic stripe emulator, an image, a computer chip, a smart-card interface, a wireless interface, an optical interface, a communications interface, a radio frequency identification (RFID), a hologram, a logo, an identification number, a company name, a user name, an owners name, a design, an image or a combination thereof.

3. The antimicrobial card as recited in claim 1, wherein the card comprises an identification card, a credit card, a debit card, an insurance card, a transaction card, ATM card, a supermarket card, a club card, a lost and found key chain program card, a library card, a health club card, a membership card, a rental car loyalty programs card, a hotel loyalty programs card, a prepaid phone card, a video rental card, an access card, an identification card, a driver's license, a firearm license, a physical access security card, a mini-card, a security card, a stored value card, a vendor-specific card or a combination thereof.

4. The antimicrobial card as recited in claim 1, wherein the one or more antimicrobial agents comprise between about 0.05 and 3.0%.

5. The antimicrobial card as recited in claim 1, wherein the one or more polymers are selected from acrylonitrile-butadiene-styrene, allyl resin, cellulosic, epoxy, ethylene vinyl alcohol, fluoroplastics, liquid crystal polymer, melamine formaldehyde, phenol-formaldehyde plastic, polyacetal, polyacrylates, polyacrylonitrile, polyamide, Nylon, polyamide-imide, polyaryletherketone, polybutadiene, polybutylene, polycarbonate, polydicyclopentadiene, polyketone, polyester, polyetheretherketone, polyetherimide, polyethersulfone, polyethylene, polyethylenechlorinates, polyimide, polymethylpentene, polyphenylene oxide, polyphenylene sulfide, polyphthalamide, polypropylene, polystyrene, polysulfone, polyurethane, polyvinylchloride, polyvinylidene chloride, silicon, thermoplastic elastomers, ethylene and combinations and mixtures thereof.

6. The antimicrobial card as recited in claim 1, wherein the one or more antimicrobial agents comprise 2,4,4'-trichloro-2'-hydroxydiphenyl ether; silver zeolite; silver glass; 4-t-butylamino-6-cyclopropylamino-2-methylthio-s-triazine; thiabendazole, 2-(4-thiazolyl) benzimidazole; dichloro-octyl-isothiazolone; octyl-isothiazolone; 10,10-oxybisphenoxarsine; tebuconazole; tolnaflate; zinc bis-(2-pyridinethiol-1-oxide) and mixtures and combinations thereof.

7. An antimicrobial card comprising:
a card made from an antimicrobial polymereric material comprising one or more polymers selected from styrene, polyvinyl chloride and laminated polyvinyl chloride, and between about 0.05 and 3.0% of one or more antimicrobial agents that affect the growth of a bacteria, a fungi, a virus or a combination thereof selected from 2,4,4'-trichloro-2'-hydroxydiphenyl ether, silver zeolite, silver glass, 4-t-butylamino-6-cyclopropylamino-2-methylthio-s-triazine, thiabendazole, 2-(4-thiazolyl)benzimidazole, dichloro-octyl-isothiazolone, octyl-isothiazolone, 10,10-oxybisphenoxarsine, tebuconazole, tolnaflate, zinc bis-(2-pyridinethiol-1-oxide) and mixtures and combinations thereof such that the antimicrobial polymeric material is at least on the exterior of the card; and
one or more identifiers disposed on or within the card.

8. The antimicrobial card as recited in claim 7, wherein the card comprises an identification card, a credit card, a debit card, an insurance card, a transaction card, ATM card, a supermarket card, a club card, a lost and found key chain program card, a library card, a health club card, a membership card, a rental car loyalty programs card, a hotel loyalty programs card, a prepaid phone card, a video rental card, an access card, an identification card, a driver's license, a firearm license, a physical access security card, a mini-card, a security card, a stored value card, a vendor-specific card or a combination thereof.

9. The antimicrobial card as recited in claim 7, wherein the identifiers comprise a barcode, a magnetic stripe, a magnetic stripe emulator, an image, a computer chip, a smart-card interface, a wireless interface, an optical interface, a communications interface, a radio frequency identification (RFID), a hologram, a logo, an identification number, a company name, a user name, an owners name, a design, an image or a combination thereof.

10. A method of reducing the growth of bacteria, fungi, or virus on a card composing the steps of:
forming a card comprising one or more polymers and one or more antimicrobial agents, wherein the card comprises a magnetic stripe and the antimicrobial polymeric material is at least on an exterior of the card.

11. The method recited in claim 10, wherein the antimicrobial card further comprises a barcode, an image, a computer chip, a radio frequency identification (RFID), a hologram, an identification number or a combination thereof.

12. The method as recited in claim 10, wherein the one or more antimicrobial agents comprise between about 0.05 and 3.0%.

13. The method as recited in claim 10 wherein the one or more polymers are selected from acrylonitrile-butadiene-styrene, allyl resin, cellulosic, epoxy, ethylene vinyl alcohol, fluoroplastics, liquid crystal polymer, melamine formaldehyde, phenol-formaldehyde plastic, polyacetal, polyacrylates, polyacrylonitrile, polyamide, Nylon, polyamide-imide, polyaryletherketone, polybutadiene, polybutylene, polycarbonate, polydicyclopentadiene, polyketone, polyester, polyetheretherketone, polyetherimide, polyethersulfone, polyethylene, polyethylenechlorinates, polyimide, polymethylpentene, polyphenylene oxide, polyphenylene sulfide, polyphthalamide, polypropylene, polystyrene, polysulfone, polyurethane, polyvinylchloride, polyvinylidene chloride, silicon, thermoplastic elastomers, ethylene and combinations and mixtures thereof.

14. The method as recited in claim 10, wherein the card comprises an identification card, a credit card, a debit card, an insurance card, a transaction card, ATM card, a supermarket card, a club card, a lost and found key chain program card, a library card, a health club card, a membership card, a rental car loyalty programs card, a hotel loyalty programs card, a prepaid phone card, a video rental card, an access card, an identification card, a driver's license, a firearm license, a physical access security card, a mini-card, a security card, a stored value card, a vendor-specific card or a combination thereof.

15. The method as recited in claim 10, wherein the one or more antimicrobial agents comprise 2,4,4'-trichloro-2'-hydroxydiphenyl ether, silver zeolite, silver glass, 4-t-butylamino-6-cyclopropylamino-2-methylthio-s-triazine, thiabendazole, 2-(4-thiazolyl)benzimidazole, dichloro-octyl-isothiazolone, octyl-isothiazolone, 10,10-oxybisphenoxarsine, tebuconazole, tolnaflate, zinc bis-(2-pyridinethiol-1-oxide) and mixtures and combinations thereof.

16. An antimicrobial token comprising:
a token made from an antimicrobial polymereric material comprising one or more polymers and one or more antimicrobial agents that affect the growth of bacteria, fungi, virus or a combination thereof on the token such that the antimicrobial polymeric material is at least on an exterior of the token; and
one or more identifiers disposed on or within the token.

17. The antimicrobial token as recited in claim 16, wherein the token comprises a gambling chip.

18. The antimicrobial token as recited in claim 16, wherein the one or more antimicrobial agents comprise between about 0.05 and 3.0%.

19. The antimicrobial token as recited in claim 16, wherein the one or more polymers are selected from acrylonitrile-butadiene-styrene, allyl resin, cellulosic, epoxy, ethylene vinyl alcohol, fluoroplastics, liquid crystal polymer, melamine formaldehyde, phenol-formaldehyde plastic, polyacetal, polyacrylates, polyacrylonitrile, polyamide, Nylon, polyamide-imide, polyaryletherketone, polybutadiene, polybutylene, polycarbonate, polydicyclopentadiene, polyketone, polyester, polyetheretherketone, polyetherimide, polyethersulfone, polyethylene, polyethylenechlorinates, polyimide, polymethylpentene, polyphenylene oxide, polyphenylene sulfide, polyphthalamide, polypropylene, polystyrene, polysulfone, polyurethane, polyvinylchloride, polyvinylidene chloride, silicon, thermoplastic elastomers, ethylene and combinations and mixtures thereof.

20. The antimicrobial token as recited in claim 16, wherein the one or more antimicrobial agents comprise 2,4,4'-trichloro-2'-hydroxydiphenyl ether, silver zeolite, silver glass, 4-t-butylamino-6-cyclopropylamino-2-methylthio-s-triazine, thiabendazole, 2-(4-thiazolyl)benzimidazole, dichloro-octyl-isothiazolone, octyl-isothiazolone, 10,10- oxybisphenoxarsine, tebuconazole, tolnaflate, zinc bis-(2-pyridinethiol-1-oxide) and mixtures and combinations thereof.

21. An antimicrobial badge holder comprising:
a badge holder made from made from an antimicrobial polymereric material comprising one or more polymers and one or more antimicrobial agents that affect the growth of bacteria, fungi, virus or a combination thereof on the badge holder such that the antimicrobial polymeric material is at least on an exterior of the badge holder; and
one or more identifiers disposed on or within the badge holder.

22. The antimicrobial badge holder as recited in claim 21, wherein the one or more antimicrobial agents comprise between about 0.05 and 3.0%.

23. The antimicrobial badge holder as recited in claim 21, wherein the one or more polymers are selected from acrylonitrile-butadiene-styrene, allyl resin, cellulosic, epoxy, ethylene vinyl alcohol, fluoroplastics, liquid crystal polymer, melamine formaldehyde, phenol-formaldehyde plastic, polyacetal, polyacrylates, polyacrylonitrile, polyamide, Nylon, polyamide-imide, polyaryletherketone, polybutadiene, polybutylene, polycarbonate, polydicyclopentadiene, polyketone, polyester, polyetheretherketone, polyetherimide, polyethersulfone, polyethylene, polyethylenechlorinates, polyimide, polymethylpentene, polyphenylene oxide, polyphenylene sulfide, polyphthalamide, polypropylene, polystyrene, polysulfone, polyurethane, polyvinylchloride, polyvinylidene chloride, silicon, thermoplastic elastomers, ethylene and combinations and mixtures thereof.

24. The antimicrobial badge holder as recited in claim 21, wherein the one or more antimicrobial agents comprise 2,4,4'-trichloro-2'-hydroxydiphenyl ether, silver zeolite, silver glass, 4-t-butylamino-6-cyclopropylamino-2-methylthio-s-triazine, thiabendazole, 2-(4-thiazolyl)benzimidazole, dichloro-octyl-isothiazolone, octyl-isothiazolone, 10,10-oxybisphenoxarsine, tebuconazole, tolnaflate, zinc bis-(2-pyridinethiol-1-oxide) and mixtures and combinations thereof.

25. The antimicrobial card as recited in claim 1, wherein the antimicrobial polymeric material comprises a coating or covering over the exterior of the card.

26. The antimicrobial card as recited in claim 1, wherein the card is substantially made from the antimicrobial polymeric material.

27. The antimicrobial card as recited in claim 7, wherein the antimicrobial polymeric material comprises a coating or covering over the exterior of the card.

28. The antimicrobial card as recited in claim 7, wherein the card is substantially made from the antimicrobial polymeric material.

29. The method as recited in claim 10, wherein the antimicrobial polymeric material comprises a coating or covering over the exterior of the card.

30. The method as recited in claim 10, wherein the card is substantially made from the antimicrobial polymeric material.

31. The antimicrobial token as recited in claim 16, wherein the antimicrobial polymeric material comprises a coating or covering over the exterior of the token.

32. The antimicrobial token as recited in claim 16, wherein the token is substantially made from the antimicrobial polymeric material.

33. The antimicrobial badge holder as recited in claim 21, wherein the antimicrobial polymeric material comprises a coating or covering over the exterior of the badge holder.

34. The antimicrobial badge holder as recited in claim 21, wherein the badge holder is substantially made from the antimicrobial polymeric material.

* * * * *